United States Patent
Mathissen et al.

(10) Patent No.: US 10,352,854 B2
(45) Date of Patent: Jul. 16, 2019

(54) MOTOR VEHICLE HAVING DUST SENSOR FOR REDUCING DUST RESUSPENSION

(71) Applicant: FORD GLOBAL TECHNOLOGIES, LLC, Dearborn, MI (US)

(72) Inventors: Marcel Mathissen, Wurselen (DE); Volker Scheer, Roetgen (DE); Rainer Vogt, Aachen (DE)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 15/372,901

(22) Filed: Dec. 8, 2016

(65) Prior Publication Data

US 2017/0167975 A1  Jun. 15, 2017

(30) Foreign Application Priority Data

Dec. 9, 2015  (DE) .................. 10 2015 224 725

(51) Int. Cl.
| | | |
|---|---|---|
| *B60Q 9/00* | (2006.01) | |
| *B60S 1/46* | (2006.01) | |
| *B60S 1/68* | (2006.01) | |
| *G01N 15/06* | (2006.01) | |
| *G01N 21/47* | (2006.01) | |

(52) U.S. Cl.
CPC ........... *G01N 21/47* (2013.01); *B60Q 9/00* (2013.01); *B60S 1/46* (2013.01); *B60S 1/68* (2013.01); *G01N 2015/0693* (2013.01)

(58) Field of Classification Search
CPC ............... B60Q 9/00; B60S 1/46; B60S 1/68
USPC .......................................................... 701/70
See application file for complete search history.

(56) References Cited

U.S. PATENT DOCUMENTS

| | | |
|---|---|---|
| 4,102,426 A | 7/1978 | Walden |
| 5,517,298 A | 5/1996 | Devenport |
| 6,401,520 B1 * | 6/2002 | Volkwein ............ G01N 1/2205 |
| | | 73/28.03 |
| 6,592,642 B2 | 7/2003 | Maricq et al. |
| | (Continued) | |

FOREIGN PATENT DOCUMENTS

| | | |
|---|---|---|
| AT | 409039 B | 5/2002 |
| CN | 2052369 U | 2/1990 |
| | (Continued) | |

OTHER PUBLICATIONS

German Search Report dated Oct. 12, 2016 for German Application No. 102015224719.8, 5 pgs.

(Continued)

*Primary Examiner* — Maceeh Anwari
(74) *Attorney, Agent, or Firm* — Frank A. MacKenzie; Brooks Kushman P.C.

(57) ABSTRACT

The disclosure relates to a motor vehicle comprising a dust sensor. The dust sensor is a scattered light photometer according to the disclosure. The scattered light photometer measures the dust load of the air in a region of the motor vehicle in which resuspended or emitted dust has a tendency to occur during travel. In addition, the motor vehicle contains a device for dust reduction, which receives measured data from the scattered light photometer, and decides, on the basis of the measured data, whether measures are to be taken against dust resuspension or dust emission. The device takes corresponding measures if the dust load exceeds a threshold value.

15 Claims, 1 Drawing Sheet

(56) References Cited

U.S. PATENT DOCUMENTS

| | | |
|---|---|---|
| 7,103,460 B1 | 9/2006 | Breed |
| 8,167,098 B2 | 5/2012 | Jessberger |
| 8,497,476 B2 | 7/2013 | Hatakeyama et al. |
| 2004/0255425 A1 | 12/2004 | Arai et al. |
| 2009/0224084 A1 | 9/2009 | Hoisington et al. |
| 2009/0300870 A1* | 12/2009 | Riach .................. A47L 9/1608 15/320 |
| 2011/0160920 A1 | 6/2011 | Orr et al. |
| 2012/0268582 A1 | 10/2012 | Rothenhausler |
| 2013/0047703 A1 | 2/2013 | Stengel et al. |
| 2014/0054119 A1 | 2/2014 | Hummel et al. |
| 2014/0054120 A1 | 2/2014 | Hummel et al. |
| 2014/0054121 A1 | 2/2014 | Hummel et al. |
| 2014/0263720 A1 | 9/2014 | Travaglini |
| 2015/0353291 A1 | 12/2015 | Teichrob et al. |
| 2016/0135655 A1 | 5/2016 | Ahn et al. |
| 2016/0280160 A1 | 9/2016 | MacNeille et al. |

FOREIGN PATENT DOCUMENTS

| | | |
|---|---|---|
| CN | 103741629 A | 4/2014 |
| CN | 203729238 U | 7/2014 |
| CN | 204086082 U | 1/2015 |
| DE | 69009605 T2 | 9/1994 |
| DE | 10149468 A1 | 4/2003 |
| DE | 10311800 A1 | 9/2004 |
| DE | 10329961 A1 | 1/2005 |
| DE | 10329931 A1 | 2/2005 |
| DE | 202005005673 U1 | 9/2005 |
| DE | 202006004522 U1 | 6/2006 |
| DE | 202006019335 U1 | 4/2008 |
| DE | 202007000246 U1 | 5/2008 |
| DE | 102009054194 A1 | 5/2011 |
| DE | 102010002424 A1 | 9/2011 |
| DE | 102016105135 A1 | 9/2016 |
| JP | H09242500 A | 9/1997 |
| JP | 1172327 A | 3/1999 |
| JP | 2004185399 A | 7/2004 |
| JP | 2008302803 A * | 12/2008 |
| JP | 2008302803 A | 12/2008 |
| KR | 100896922 B1 | 5/2009 |
| KR | 101511663 B1 | 4/2015 |
| WO | 03035206 A2 | 5/2003 |

OTHER PUBLICATIONS

German Search Report dated Oct. 18, 2016 for German Application No. 102015224725.2, 6 pgs.

* cited by examiner

MOTOR VEHICLE HAVING DUST SENSOR FOR REDUCING DUST RESUSPENSION

CROSS-REFERENCE TO RELATED APPLICATIONS

This application claims foreign priority benefits under 35 U.S.C. § 119(a)-(d) to DE 10 2015 224 725.2 filed Dec. 9, 2015, which is hereby incorporated by reference in its entirety.

TECHNICAL FIELD

The disclosure relates to a motor vehicle having a dust sensor and a method for reducing dust resuspension or dust emission by a motor vehicle.

BACKGROUND

Traffic-related particle emissions, not resulting from exhaust gases, but rather from abrasion of brakes, tires, clutches, road coverings, etc. and also from resuspension of road dust, contribute substantially to air pollution. Exhaust gas particle emissions are expected to decrease as a result of stricter limiting values, but the other traffic-related particle emissions will increase as a result of greater traffic volume and could come into the focus of future regulations. According to data of the German Federal environmental office, it may be expected that exhaust gas particle emissions in the year 2020 will still make up approximately 18% of all traffic-related fine dust emissions, wherein the term fine dust refers to the particles, which are considered to be especially harmful to health, having aerodynamic diameters less than 10 μm. The remaining 82% are emissions not caused by exhaust gas, but rather by wear. This shows the increasing significance of the particle emissions, which are not caused by exhaust gas.

Technologies, for example, shields, fans, and dust collectors, are known especially for reducing brake dust emissions.

WO 03/035206 A2 discloses a motor vehicle having a particle analyzer installed therein. This particle analyzer, which is supposed to also be able to count the particles, is a very complex device, which is only used for test travel.

U.S. Pat. No. 5,517,298 A discloses a device for measuring the movement of transparent gases or liquids by illuminating entrained small solid or liquid particles and measuring the velocity thereof by velocimetry.

DE 10 329 961 A1 discloses an integrated fine dust suction device for vehicles, using which fine dust can be filtered out of the ambient air and collected for scientific studies and which can also be analyzed during the collection using an aerosol spectrometer as a dust meter, wherein the measured data can be relayed via radio.

Motor vehicles have also already been proposed, wherein the ambient air is to be filtered of fine dust during travel.

Thus, DE 20 2006 019 335 U1 discloses a fine dust suction device for vehicles, wherein the fresh air supplied to the vehicle interior can be filtered of fine dust, but which the fine dust content in the ambient air can also be reduced, in order to maintain fine dust limiting values prescribed by law.

DE 20 2006 004 522 U1 discloses a fine dust filter, which operates using electrical and/or magnetic separation, and which is arranged between an air intake grill and a radiator, to filter the ambient air flowing through therein of fine dust, as well as that fine dust which has been emitted or resuspended by other vehicles.

DE 20 2005 005 673 U1 discloses an external air filter, which is mounted under a bumper, for motor vehicles for general reduction of air pollution.

Such systems could only effectively reduce fine dust in the environment if they have been installed in a very large number of vehicles, and the effort for cleaning the many filters and/or for disposing of the collected dust would also be extreme, particularly also because comparatively coarse dust, which is not actually harmful, would be collected and the filters would fill up rapidly.

DE 10 2009 054 194 A discloses a vehicle having a heads-up display and a camera introduced into the beam path thereof, from the image data of which rain or dirt on the windshield can also be recognized.

JP H09 242 500 A discloses an environmental measuring vehicle having a dust concentration sensor arranged on the roof.

SUMMARY

The disclosure is based on the object of being able to reduce dust resuspension and/or dust emission by motor vehicles in a more targeted manner.

According to the disclosure, the dust sensor is a scattered light photometer, which measures the dust load of the air in a region of the motor vehicle in which, for example, dust resuspended by the tires or, for example, emitted by the brakes has a tendency to occur during travel. On the basis of the measured data of the scattered light photometer, it can be decided whether any dust-reducing measures are to be taken, and if necessary which ones.

A relatively simple scattered light photometer is sufficient for the disclosure, which only supplies a coarse estimated value for the fine dust concentration in the region of the motor vehicle observed thereby.

The disclosure enables a resuspension or release of fine dust, which is recognized by sensors to be counteracted in a targeted manner, for example, by temporary influencing measures on the travel velocity and/or by targeted, but temporary air purification measures in the affected regions.

According to one study about road conditions in central Europe, the largest part of the particle emissions that are not caused by exhaust gas occur on only 10% of the road network having particularly high levels of pollutant introduction. In addition, brake dust is only released in particularly large quantities in a few situations.

The disclosure therefore enables the restrictions and the effort, which are linked to the reduction of resuspension and/or release of fine dust to be kept within limits, because these measures can be restricted to phases of particularly high levels of dust resuspension and/or emission. A comparatively large benefit for the environment can be achieved using this comparatively little effort.

The scattered light photometer is preferably attached in a wheel housing, to an underbody, or to a bumper of the motor vehicle. Multiple scattered light photometers can also be attached at various such positions.

Furthermore, scattered light photometers and dust reduction devices can be attached at different positions on the vehicle. Thus, for example, a photometer on a front wheel can supply useful items of information for a dust reduction device further to the rear on the vehicle.

The estimated values for the fine dust concentration supplied by the scattered light photometer can be filtered, in order to only take the strongest dust loads into consideration.

The obtained data can be used as input parameters for a device for dust reduction. The following come into consideration for this purpose:

- a water-based dust reduction system known per se, which sprays water onto the roadway and/or the tires of the vehicle, but only when high dust concentrations are measured, so that the water reservoir required for this purpose does not have to be very large;
- an electrostatically operating dust reduction system known per se, which is also only active when high dust concentrations are measured, so that the container required for precipitated dust does not have to be very large;
- a dust reduction system based on conventional filter media, in particular felt, nonwoven material, artificial fibers, fabric filters, or similar media, in which the airflow is only conducted via the filter if high dust emissions are to be expected, so that the filter service life is significantly extended;
- a human-machine interface, which requests or suggests that the driver reduce the velocity to decrease dust resuspension, because this increases disproportionately with the travel velocity. A suggestion to reduce the velocity can be given, for example, in the manner of known visual displays for economic driving, wherein green stands for low, yellow for moderate, and red for high dust emissions;
- a forced velocity restriction of the vehicle if high dust concentrations originating from misuse are measured, for example, in the event of excessively rapid travel with spiked tires;
- a cloud service of a vehicle ad-hoc network for vehicle-to-vehicle communication, onto which the obtained data can be uploaded together with geoposition data of the vehicle and which prepares a dust load map from the collected data of a very large number of vehicles, which represents a real-time map of the potential for dust load. The mass data obtained in this manner can be provided to the owners of road infrastructure or those responsible for this purpose, who can then take suitable countermeasures, for example, establishing local velocity restrictions for all vehicles or only for vehicles without dust reduction system and/or to have affected road sections cleaned more frequently.

Exemplary embodiments are described hereafter on the basis of the drawings. In the figures:

DETAILED DESCRIPTION

As required, detailed embodiments of the present disclosure are disclosed herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Figure 1:
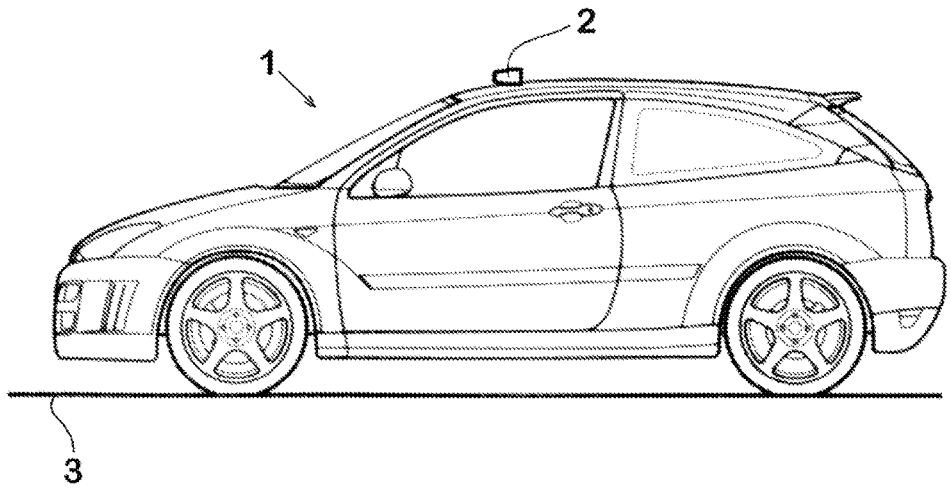
FIG. 1 shows a schematic side view of a motor vehicle having a dust sensor.

The motor vehicle 1 shown in FIG. 1 has a scattered light photometer 2 in a wheel housing. The scattered light photometer measures the concentration of dust particles prevailing in the wheel housing, which are resuspended from a roadway surface 3 or emitted by the corresponding brake.

Figure 2:
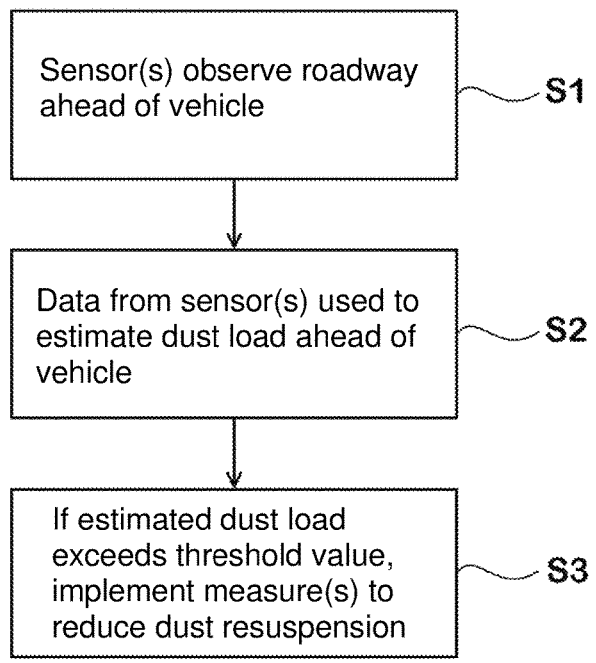
FIG. 2 shows a flow chart of a method for reducing dust resuspension or dust emission by a motor vehicle.

With reference to FIG. 2 as well, in travel operation of the motor vehicle 1, the dust concentration in the wheel housing is monitored (step S1) and estimated (step S2) by means of the scattered light photometer 2. If the estimated value for the dust concentration in the wheel housing exceeds a threshold value, and also only then, measures are taken, activated via a device, to reduce dust resuspension (step S3), for example, to bind or filter out dust and/or to act on a reduction of the travel velocity of the vehicle.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure.

What is claimed is:

1. A vehicle comprising:
    a scattered light photometer that measures a dust load of air attached to a bumper where resuspended dust occurs during travel; and
    a dust reduction device configured to receive measured data of the dust load from the scattered light photometer, and, in response to the measured data, determine a measure that reduces dust resuspension, and initiate the measure, wherein the measure comprises at least spraying water toward a region adjacent to the bumper.

2. The vehicle as claimed in claim 1, wherein the measured data of the scattered light photometer indicates a dust particle concentration.

3. The vehicle as claimed in claim 1, wherein the dust reduction device includes a human-machine interface to communicate the measure.

4. The vehicle as claimed in claim 1, wherein the dust reduction device includes a cloud service of a network for vehicle-to-vehicle communication.

5. A method for reducing dust emission by a motor vehicle comprising:
    monitoring a dust load of air, via a plurality of dust sensors, in a plurality of regions of an underbody structure where resuspended dust occurs during vehicle travel;
    estimating, based on data from the plurality of dust sensors, the dust load in each of the regions; and
    in response to the dust load in each of the regions exceeding a threshold value, binding dust using sprayed water at one of the regions at each of the regions.

6. The method as claimed in claim 5, wherein monitoring the dust load via the plurality of dust sensors includes measuring a dust particle concentration in the regions.

7. The method as claimed in claim 6 further comprising filtering dust out of the air electrostatically at another of the regions.

8. The method as claimed in claim 6 further comprising reducing a travelling velocity of the motor vehicle.

9. The method as claimed in claim 5 further comprising prompting, via a visual display, the measures.

10. The method as claimed in claim 5 further comprising prompting, via a human machine interface, the measures in at least three colors.

11. The method as claimed in claim 5 further comprising communicating, via a cloud service of a vehicle ad-hoc network, with an adjacent motor vehicle to prepare a dust load map of the dust load.

12. An electrostatic dust reduction system comprising:
 a dust sensor attached at a wheel housing of a vehicle and configured to measure a dust load in the region, the dust load being defined by a dust particle concentration; and
 a dust reduction device configured to, in response to the dust particle concentration indicating that the dust load exceeds a threshold value, open a water reservoir configured to spray water onto vehicle tire to reduce dust resuspension.

13. The electrostatic dust reduction system as claimed in claim 12, wherein the dust sensor is a scattered light photometer.

14. The electrostatic dust reduction system as claimed in claim 12, wherein the device is further configured to suggest, via a human machine interface, a reduction of velocity to decrease dust resuspension.

15. The electrostatic dust reduction system as claimed in claim 12 further comprising an additional dust sensor attached at a second region different from the region, the additional dust sensor configured to measure an additional dust load in the second region, the additional dust load being defined by a dust particle concentration at the second region.

* * * * *